(12) United States Patent
Mingione et al.

(10) Patent No.: US 10,076,648 B2
(45) Date of Patent: Sep. 18, 2018

(54) ANTISEPTIC APPLICATOR

(71) Applicant: CAREFUSION 2200, INC., San Diego, CA (US)

(72) Inventors: Louis P. Mingione, Chicago, IL (US); Charlie Beuchat, Anaheim Hills, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 0 days.

(21) Appl. No.: 15/881,314

(22) Filed: Jan. 26, 2018

(65) Prior Publication Data

US 2018/0147398 A1    May 31, 2018

Related U.S. Application Data

(63) Continuation of application No. 14/566,608, filed on Dec. 10, 2014.

(51) Int. Cl.
*A61M 35/00*    (2006.01)
*A61F 13/40*    (2006.01)

(52) U.S. Cl.
CPC ........ *A61M 35/006* (2013.01); *A61M 35/003* (2013.01)

(58) Field of Classification Search
CPC combination set(s) only.
See application file for complete search history.

(56) References Cited

U.S. PATENT DOCUMENTS

| | | | |
|---|---|---|---|
| 1,332,985 A | * | 3/1920 | Jarrett ................. B01F 11/0065 137/13 |
| 3,757,782 A | | 9/1973 | Aiken |
| 4,415,288 A | | 11/1983 | Gordon et al. |
| 4,498,796 A | | 2/1985 | Gordon et al. |
| 4,784,506 A | | 11/1988 | Koreska et al. |
| 5,288,159 A | | 2/1994 | Wirt |
| 5,308,180 A | | 5/1994 | Pournoor et al. |
| 5,435,660 A | | 7/1995 | Wirt |
| 5,445,462 A | | 8/1995 | Johnson et al. |
| 5,658,084 A | | 8/1997 | Wirt |
| 5,769,552 A | | 6/1998 | Kelley et al. |
| 5,772,346 A | | 6/1998 | Edwards |
| 5,775,826 A | * | 7/1998 | Miller .................... A45D 34/04 401/132 |

(Continued)

FOREIGN PATENT DOCUMENTS

CN    103751904 A    4/2014
WO    WO 03/101370 A1    12/2003

*Primary Examiner* — David Walczak
(74) *Attorney, Agent, or Firm* — Arent Fox LLP

(57) ABSTRACT

An applicator assembly includes a plurality of ampoules formed of a frangible material and containing liquid to be applied, a container having a proximal end, a distal end, and an interior portion defining a chamber adapted to receive the plurality of ampoules, an application member attached to the distal end of the container; and at least one actuator projecting from the container, wherein the at least one actuator is actuatable to independently fracture the plurality of ampoules, thereby independently releasing the liquid into the application member. The at least one actuator may be moveable from a first position to a second position, the applicator having a smaller profile when the actuator is in the second position than when the actuator is in the first position.

12 Claims, 17 Drawing Sheets

(56) References Cited

U.S. PATENT DOCUMENTS

| | | |
|---|---|---|
| 5,791,801 A | 8/1998 | Miller |
| 5,927,884 A | 7/1999 | Kao |
| 6,371,675 B1 | 4/2002 | Hoang et al. |
| 6,488,665 B1 | 12/2002 | Severin et al. |
| 6,916,133 B2 | 7/2005 | Hoang et al. |
| 7,201,525 B2 | 4/2007 | Mohiuddin |
| 7,824,122 B2 * | 11/2010 | Flores ................. A61M 35/006 401/133 |
| 8,348,913 B2 | 1/2013 | Hoang et al. |
| 8,438,913 B2 * | 5/2013 | Richards ............. G01L 19/0645 73/716 |
| 2002/0076255 A1 | 6/2002 | Hoang et al. |
| 2004/0179888 A1 | 9/2004 | Tufts et al. |
| 2004/0254561 A1 | 12/2004 | Stenton |
| 2006/0039742 A1 | 2/2006 | Cable, Jr. et al. |
| 2008/0219750 A1 | 9/2008 | Siegel |
| 2008/0298879 A1 | 12/2008 | Chesak et al. |
| 2010/0168638 A1 | 7/2010 | Korogi et al. |
| 2011/0066121 A1 | 3/2011 | Hoang et al. |

* cited by examiner

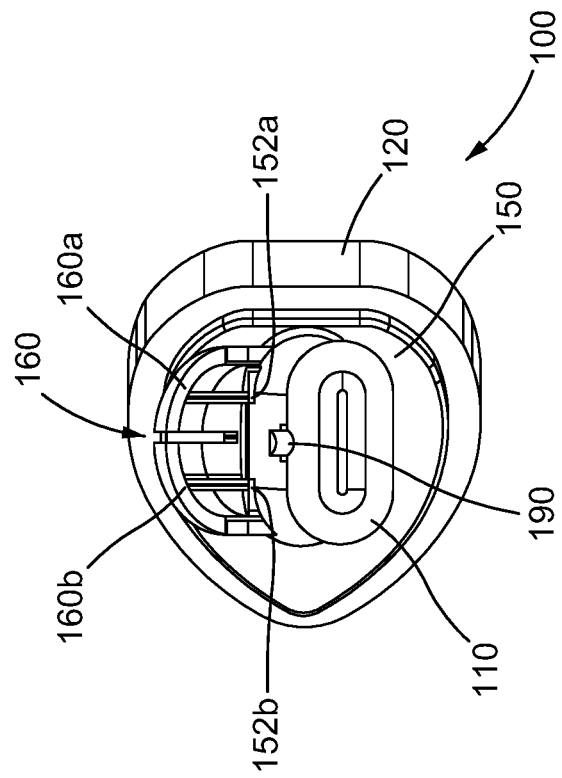
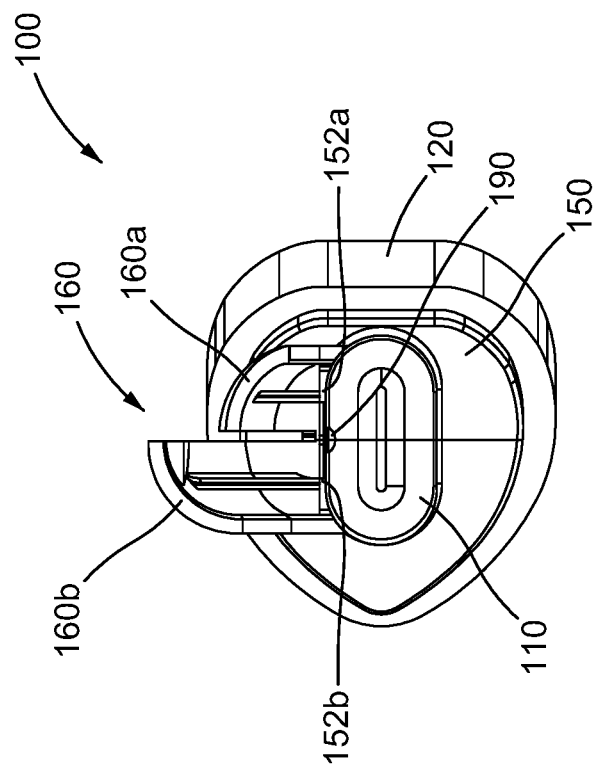

ANTISEPTIC APPLICATOR

CROSS REFERENCE TO RELATED APPLICATION

This application is a continuation of U.S. patent application Ser. No. 14/566608, filed Dec. 10, 2014, now abandon. The disclosure of the prior application is hereby incorporated by reference herein its entirety.

BACKGROUND

Field

The present disclosure relates to an antiseptic applicator and method of use thereof, and more particularly, to an antiseptic applicator that uses a compressive force to actuate release of a sealed solution, preferably an antimicrobial solution, from an ampoule.

Description of Related Art

Antiseptic applicators for the preparation of a patient prior to surgery, for example, are known and common in the prior art. Conventional applicators rely on various means of actuation to release a self-contained reservoir of antimicrobial solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742.

Other conventional applicators rely on fracturing an internally situated frangible container or ampoule through the application of a one-way directional force or a localized application of pressure. The directional force is typically applied longitudinally to one end of the ampoule by a pushing motion designed to force the ampoule to fracture under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133. All of the above listed Patent Application Publication and U.S. patents are hereby expressly incorporated by reference herein.

However, in the above-listed applicators having multiple ampoules, there is no ability for the user to control the rupturing of each ampoule independently. Furthermore, for the applicators having actuating levers, the levers increase the overall profile of the applicator, making it difficult to reach all areas of the patient. Thus, there is a need in the art for an antiseptic applicator that allows for the user to independently fracture each ampoule and a reduced profile after fracturing.

SUMMARY

In accordance with aspects of the present invention, an applicator assembly may include a plurality of ampoules formed of a frangible material and containing liquid to be applied, a container having a proximal end, a distal end, and an interior portion defining a chamber adapted to receive the plurality of ampoules, an application member attached to the distal end of the container, and at least one actuator projecting from the container, wherein the at least one actuator is actuatable to independently fracture the plurality of ampoules, thereby independently releasing the liquid into the application member.

In accordance with other aspects of the present invention, an applicator may include at least one ampoule formed of a frangible material and containing liquid to be applied, a container having a proximal end, a distal end, and an interior portion defining a chamber adapted to receive the at least one ampoule, an application member attached to the distal end of the container, and at least one actuator projecting from the container and actuatable to fracture the at least one ampoule, thereby releasing the liquid into the application member, wherein the at least one actuator is moveable from a first position to a second position, the applicator having a smaller profile when the actuator is in the second position than when the actuator is in the first position.

It will become readily apparent to those skilled in the art from the following detailed description, wherein it is shown and described only exemplary configurations of an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

BRIEF DESCRIPTION OF THE DRAWINGS

FIG. 8 is a rear perspective view of the applicator assembly of FIG. 1 after partial actuation;

FIG. 9 is a rear perspective view of the applicator assembly of FIG. 1 after full actuation;

DETAILED DESCRIPTION

Figure 1:
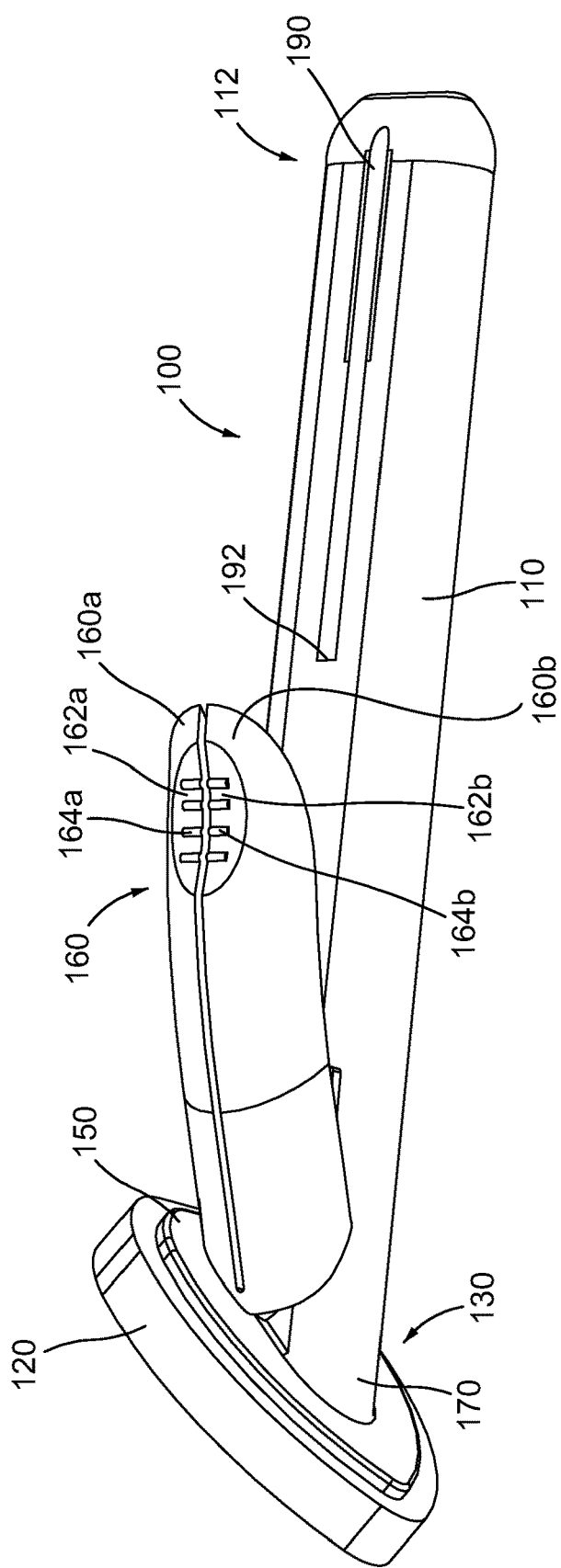
FIG. 1 is a perspective view of an antiseptic applicator assembly, in accordance with aspects of the present invention.

Various aspects of an antiseptic applicator may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator in addition to the orientation depicted in the drawings. By way of example, if an antiseptic applicator in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

The term "about" as used herein means ±10%, more preferably ±5%, and still more preferably ±1% of the provided value.

Figure 2:
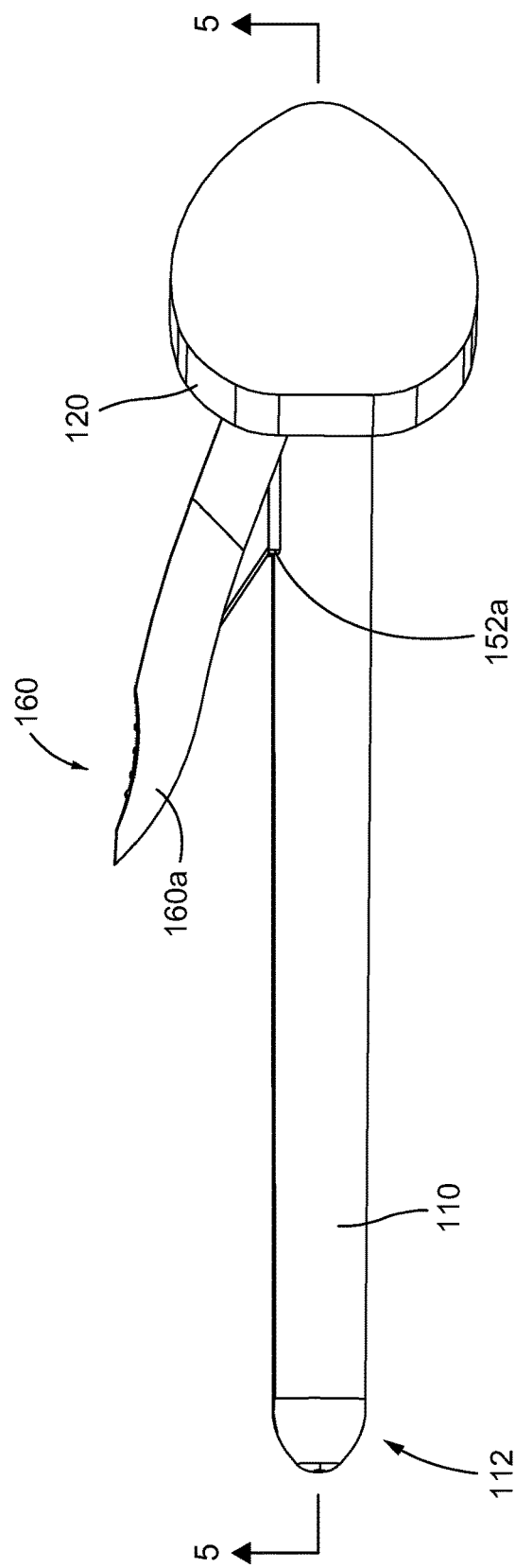
FIG. 2 is a bottom view of the applicator assembly of FIG. 1.
Figure 3:
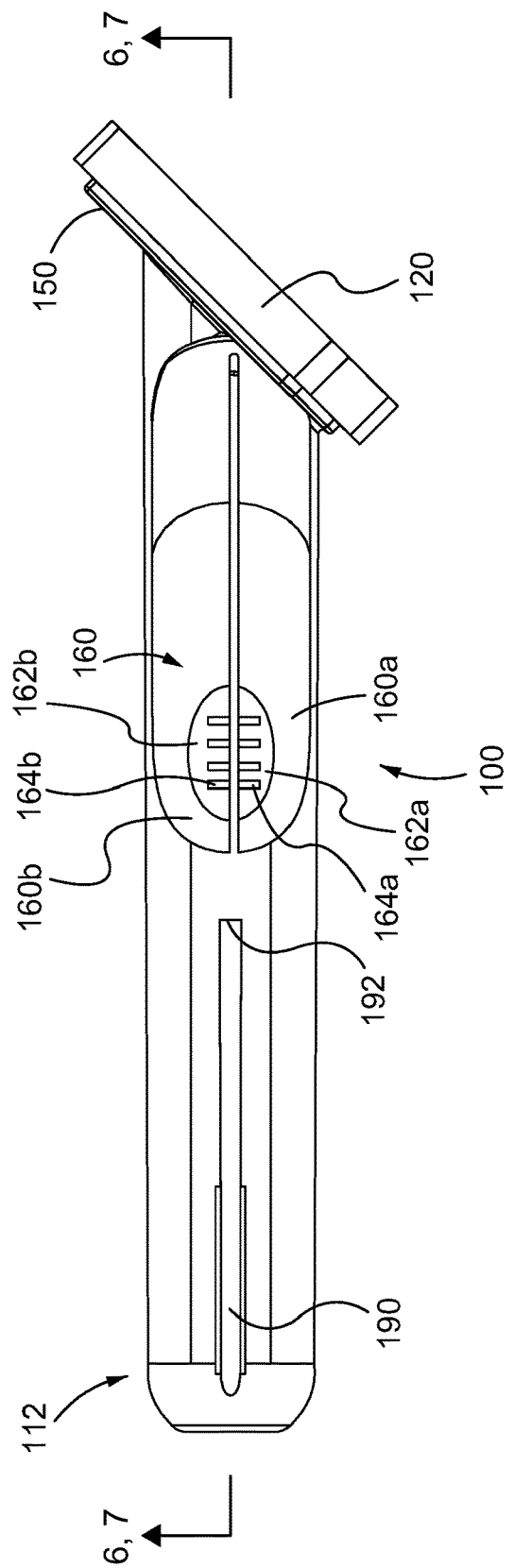
FIG. 3. is a side view of the applicator assembly of FIG. 1.
Figure 4:
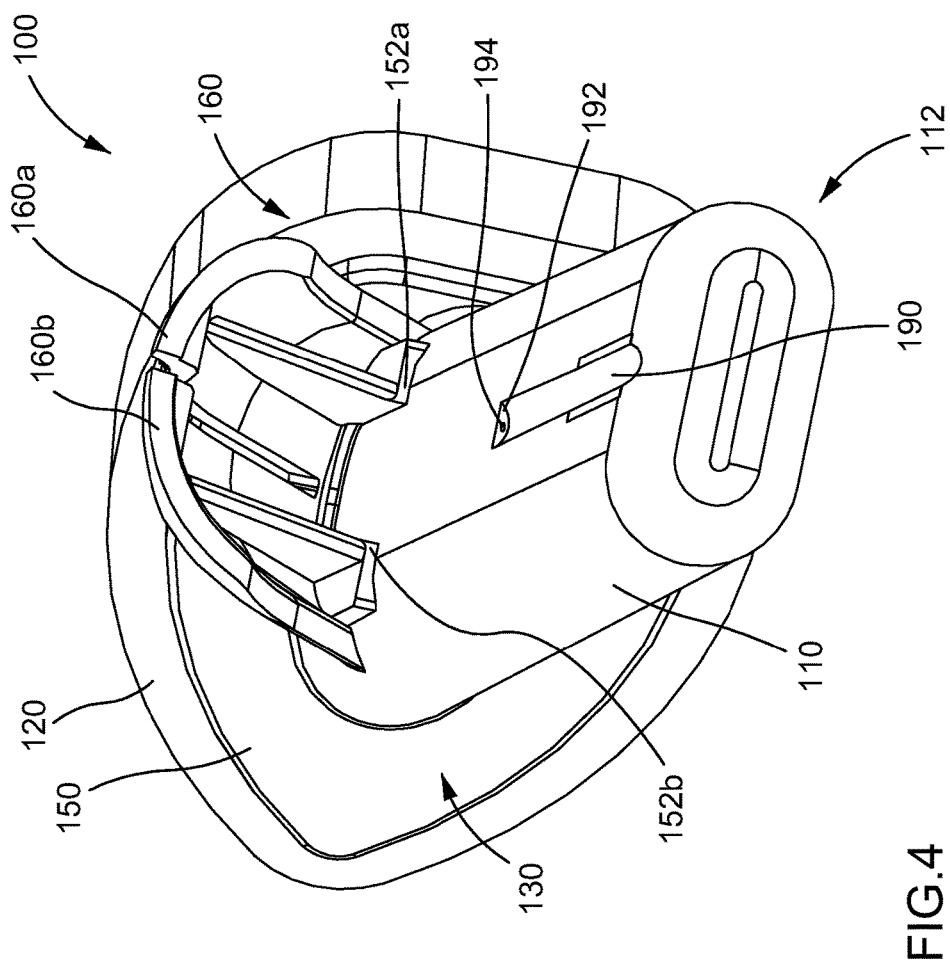
FIG. 4 is a rear perspective view of the applicator assembly of FIG. 1.
Figure 5:
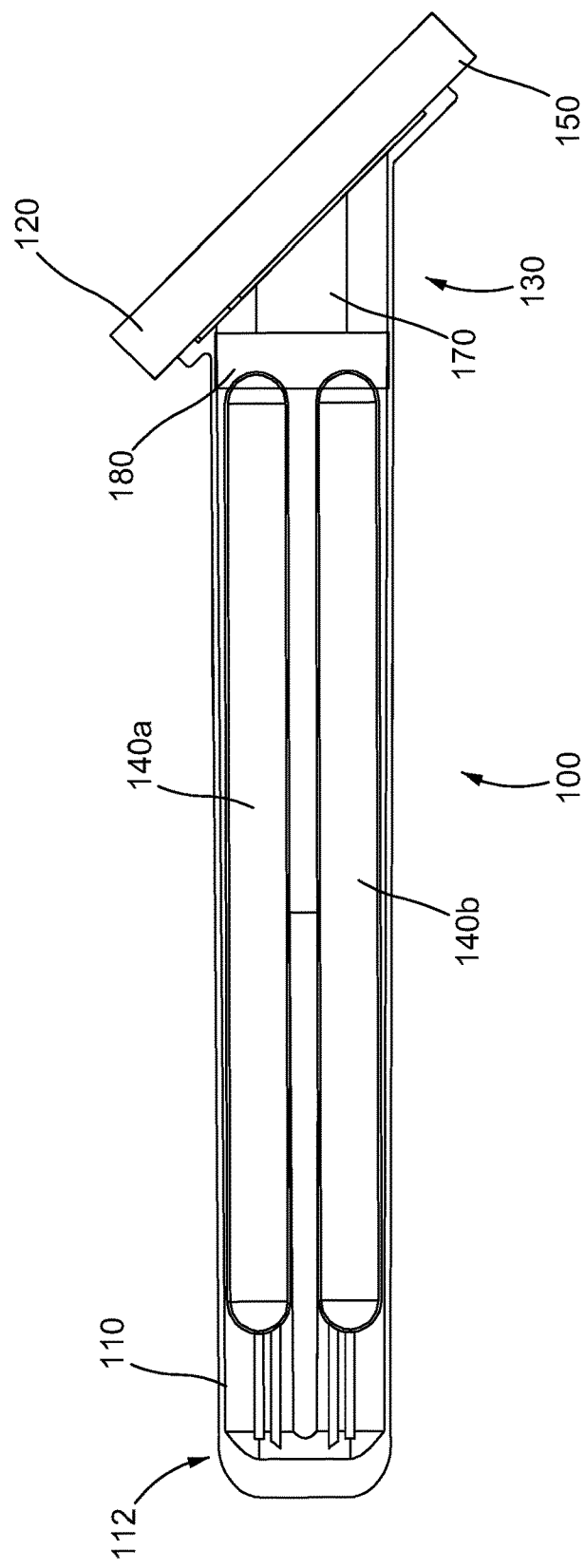
FIG. 5 is a cross section view of the applicator assembly of FIG. 1 taken along line 5-5 of FIG. 2.
Figure 6:
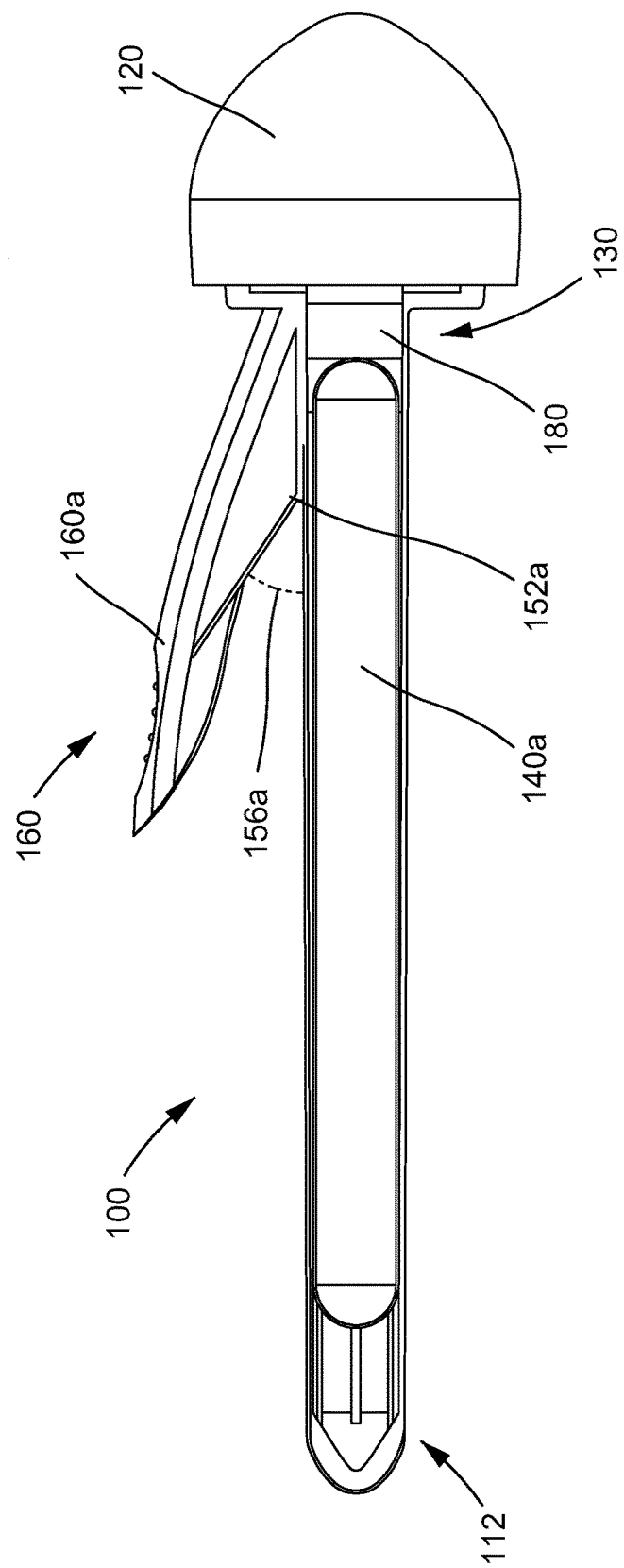
FIG. 6 is cross section view of the applicator assembly of FIG. 1 taken along line 6,7-6,7 of FIG. 3 prior to actuation.
Figure 7:
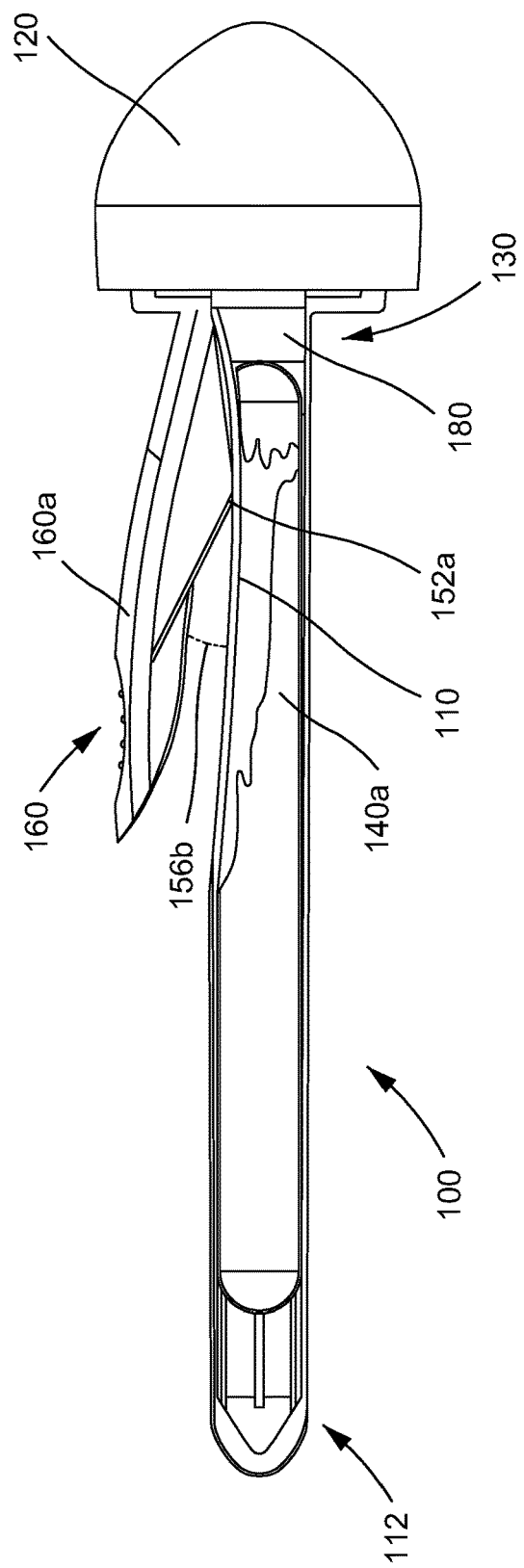
FIG. 7 is a cross section view of the applicator assembly of FIG. 1 taken along line 6,7-6,7 after actuation.

FIG. 1 shows a side perspective view of an antiseptic applicator 100 in accordance with aspects of the present invention. FIG. 2 shows a bottom view of the applicator assembly 100. FIG. 3 shows a side view of the applicator assembly of 100. FIG. 4 shows a rear perspective view of the applicator assembly 100. FIG. 5 shows a cross section view of the applicator assembly 100 taken alone line 5-5 of FIG. 2. FIG. 6 shows a cross section of the applicator assembly 100 taken along line 6,7-6,7 of FIG. 3, prior to actuation. FIG. 7 shows a cross section of the applicator assembly 100 taken along line 6,7-6,7 after actuation. As shown in FIGS. 1-7, the antiseptic applicator 100 may comprise a substantially hollow body 110, which may be cylindrical in shape, an application member 120 mounted to a distal end portion 130 of the body 110, and a plurality of ampoules 140a, 140b (FIG. 5) received within the body 110. The terms "container" and "ampoule" are used interchangeably herein. The ampoules 140a, 140b may be cylindrical or tubular in shape to position the ampoules concentrically into the body 110. In other aspects of the present invention, the body may be any variety of shapes and the container can be any variety of shape that corresponds to (e.g., is congruent to) the particular shape of the body. In an aspect of the present invention the applicator body may be formed of a single piece or it may be made of multiple pieces combined together.

The application member 120 may be formed from a foam sponge material, for example, or any suitable material that allows the controlled application of the contained solution from the ampoules 140a, 140b to a surface external to the applicator 100. The material chosen may be porous with a particular soak rate, for example, or may be provided with structural features, including slits or apertures, to direct and control the flow rate of the solution through the application member 120. The body 110 may be configured to have a mounting flange 150 at the distal end portion. The mounting flange 150 provides a surface for affixing the application member 120 to the body 110. In an aspect, the foam may be attached in any acceptable manner known in the relevant art, such as providing a novonette backing to the application member, which allows the application member to be ultrasonically welded to the body of the applicator.

The ampoules 140a, 140b are preferably a self-contained structure, formed of a suitable material that is fracturable upon application of sufficient force. Preferably, the ampoules 140a, 140b are formed of glass or plastic, although other materials are within the scope of the present invention. The wall of the ampoules may have of a thickness sufficient to contain the desired liquid during transport and storage, yet allow the container to be fractured upon the application of localized pressure. The ampoules 140a, 140b may contain medicaments, chemical compositions, cleansing agents, cosmetics, or the like. For example, the ampoules 140a, 140b may be filled with antiseptic compositions (e.g., compositions comprising one or more antiseptic molecules) preferably an antimicrobial liquid or gel composition, such as a chlorhexidine gluconate solution, octenidine dihydrochloride solution, or a povidone iodine (PVP-I) alcohol gel solution, for antiseptic application to a patient prior to surgery. The ampoules 140a, 140b may be designed to withstand various heat and chemical sterilization techniques, which may be performed sequentially with a solution filling process, in accordance with techniques that are well known in the art.

The antiseptic solution may comprise an alcoholic solvent. For example, the alcoholic solvent may be selected from the group consisting of ethanol, isopropanol, and n-propanol. The amount of solvent may be from about 40% v/v to about 90% v/v, more preferably about 50% v/v to about 80% v/v, and still more preferably about 60% v/v to about 70% v/v.

The container may contain antiseptic solution of a sufficient amount to be applied to a desired surface and have an antimicrobial effect on the desired surface. In one aspect, the desired surface is a patient's skin. It will be appreciated that the amount of antiseptic solution needed to have an antimicrobial effect on a desired surface to which the antiseptic is applied may vary. In one aspect the amount of antiseptic solution needed is 0.01-100 ml of antiseptic. More preferably, the amount of antiseptic solution need is about 0.5-60 ml and still preferably about 0.5-30 ml. Examples include 0.67, 1.0, 1.5, 3.0, 10.5, and 26.0 ml of antiseptic. However, it will be appreciated that any amount that has an antimicrobial effect on a desired surface may be utilized with the liquid applicator and method. As shown in FIG. 5, two ampoules 140a, 140b may be implemented. Thus, with two ampoules, the overall amount of antiseptic solution in the applicator 100 may be divided between the two ampoules. For example, for a 26.0 ml applicator, each ampoule may include 13.0 ml of antiseptic solution. The same principle may be implemented for any amount of solution, e.g., two ampoules of 0.5 ml together totaling 1.0 ml of solution, two ampoules of 1.5 ml together totaling 3.0 ml of solution, and so forth. It is also possible to divide the amount of solution unequally, if desired (i.e., such that one ampoule has more solution than the other ampoule). Furthermore, more than two ampoules may be implemented. For example, three, four, or more ampoules may be implemented. In these cases the amount of solution may be divided between as many ampoules as are present.

Suitable antiseptic molecules include bis-(dihydropyridinyl)-decane derivatives, octenidine salts, cationic surfactants, biguanides, and generally cationic antiseptic molecules. Preferred antiseptic agents include octenidine dihydrochloride and chlorhexidine gluconate. The concentration of the cationic antiseptic in hydroalcoholic solution may vary depending on the specific cationic antiseptic species used or the desired antimicrobial effect that is desired. For example, when using octenidine dihydrochloride or an octenidine salt the concentration may vary from about 0.0001% w/v to about 2.0% w/v, more preferably from about 0.01% w/v to about 0.5% w/v, and still more preferably from about 0.1% w/v to about 0.4% w/v. When chlorhexidine or a chlorhexidine salt is used, the concentration may be from about 0.1% w/v to about 2.5% w/v, more preferably from about 0.5% w/v to about 2.25% w/v, and still more preferably about 1.2% w/v to about 2.0% w/v. The solution may be tinted or untinted.

The applicator 100 also includes at least one actuator 160. As shown in FIGS. 1, 3, and 4, the at least one actuator may include two separate subactuators 160a, 160b. The two subactuators may abut each other. Each of the subactuators 160a, 160b may include a dimple 162a, 162b together having a shape congruent to a human thumb. Each dimple 162a, 162b may include a plurality of ridges 164a, 164b to assist the user it locating the dimple and preventing slippage of the thumb during use. The actuator 160 may comprise any mechanism configured such that, when actuated, allows the user to independently fracture the ampoules 140a, 140b. In an aspect of the present invention, the independent fracturing of the ampoules may be achieved via the subactuators 160a, 160b, which is described in more detail below. As shown in FIGS. 1, 3, and 4, the actuator 160 may comprise a lever, with the subactuators 160a, 160b comprising two separate sublevers. As shown in FIGS. 1-4, 6 and 7 the actuator 160 may project from a side portion of body 110. However, it will be appreciated that actuator 160 may project from any portion of body 110 as long as it is aligned with ampoules 140a, 140b. As best seen in FIG. 4, each of the subactuators 160a, 160b may include a contact point 152a, 152b, which apply compressive force to the body 110 when the actuator 160 is actuated. More particularly, the first subactuator 160a may include a first contact point 152a and the second subactuator 160b may include a second contact point 152b. The first contact point 152a may be aligned with the first ampoule 140a while the second contact point 152b may be aligned with the second ampoule 140b.

The actuator 160/subactuators 160a, 160b, prior to actuation, may extend at an angle 156a (FIG. 6) toward the proximal end 112 of the body 110 (e.g., the free end of the actuator/subactuators may be located closer to the proximal end of the body than the portion of the actuator connected to the body) such that when the actuator/subactuators are actuated (i.e., pressed toward the body 110), the first contact point 152a and the second contact point 152b applies compressive pressure to the body 110. The angle 156a may be from about 1° to about 60°, more preferably from about 5° to about 40°, more preferably from about 10° to about 30°, and still more preferably about 12° to about 18°. The actuation of the actuator 160 is described in more detail below. As will be described in more detail below, in an aspect of the present invention, the actuator/subactuators and the first and second contact points 152a, 152b may be configured (e.g., positioned and angled) such that, the user may choose to actuate one of the subactuators 160a, 160b independently of the other subactuator to rupture only one of the ampoules 140a, 140b or choose to actuate both subactuators 160a, 160b contemporaneously to rupture both of the ampoules together.

With the ampoules 140a, 140b mounted in the body 110, as described above, and the application member 120 mounted to close off the distal end portion 130 of the body 110, a fluid chamber 170 (FIG. 5) may be formed that extends between the application member 120 and the ampoules 140a, 140b. A fluid metering device, such as a pledget 180 (FIG. 5), for example, may be provided in the fluid chamber 170 to further control and/or direct the flow of solution from the ampoules 140a, 140b when the assembly 100 is in use. In accordance with another aspect of the present invention, the pledget 180 may contain tint to tint the solution as the solution flows from the ampoules 140a, 140b to the application member 120. In an aspect of the present invention, the pledget 180 may provide enhanced flow control and tinting of the solution as it flows from the ampoules 140a, 140b into the pledget 180. The pledget may comprise a matrix in which the tint is embedded, such as a polyolefin fiber matrix. In an aspect of the present invention, any suitable polymer material that allows for the flow of a solvent therethrough may be used. For example, the polymer may be a non-woven polyester.

The pledget 180 may have a dye incorporated therein so that the antiseptic solution becomes tinted as it passes through the pledget. The dye may be any suitable dye approved by the FDA and international authorities for use in food, drugs, and/or cosmetics (e.g., D&C and FD&C dyes). Preferred dyes may be selected from the group consisting of FD&C Blue No. 1 (Brilliant Blue FCF), FD&C Blue No. 2 (Indigo Carmine), FD&C Green No. 3 (Fast Green FCF), FD&C Red No. 3 (Erythrosine), FD&C Red No. 40 (Allura Red), FD&C Yellow No. 5 (Tartrazine), FD&C Yellow No. 6 (Sunset Yellow FCF), D&C Yellow No. 8 (Fluorescein), D&C Orange No. 4, D&C Yellow 10 (Quinoline Yellow WS), D&C Yellow No. 11, D&C Red No. 30, and combinations thereof. Other suitable dyes include beta-carotene, curcumin, iron oxide yellow, and riboflavin, iron oxide red, chlorophyll, and the like. Two or more dyes may also be combined and used together.

As shown in FIGS. 1, 3, and 4, the applicator 100 may include a trench 190 formed through the body 110. The trench 190 may extend from the proximal end 112 to a point about midway between the proximal end 112 and the distal end 130. The termination point may be positioned at other locations along the body such underneath the actuator 160. The location may be chosen to best prevent the user from accidentally covering the vent hole 192. As best seen in FIGS. 3 and 4, the trench may terminate at a vent hole 192. The vent hole may be positioned at a surface 194 that extends transverse relatively to the length of the trench 190. With the vent hole 192 located at the surface 194, it is much harder for a user to accidentally cover the vent hole 194 when operating the device.

Actuation of the assembly 100 will now be described with reference to FIGS. 6-9. Activation of the applicator 100 to release the solution and control the flow may be achieved by one handed actuation of the actuator 160. To operate the applicator 100, the operator first grasps the body 110. The user then places a thumb onto one or more of the subactuators 160a, 160b depending on the amount of fluid that the user desires to release. If the user desires to break only one of the ampoules to release an initial amount of fluid, the user will place the thumb on one of the subactuators 160a, 160b. If the user desires to release all of the fluid at once, the user will place the thumb on both of the subactuators 160a, 160b contemporaneously. As noted above the dimples 162a, 162b, and the ridges 164a, 164b will assist the user to locate the proper placement of the thumb. That is, the user will be able to feel whether the thumb is in the proper place to actuate one or both of the subactuators 160a, 160b. While thumb actuation is described above, it should also be understood that the user my grip the actuator/subactuators with the palm of the hand. As noted above FIGS. 1-4 and 6 show the location of the actuator/subactuators prior to any actuation. Prior to actuation the actuator/subactuators have an angle 156a relative to the body 110.

When the operator desires to release some or all of the fluid contained in the ampoules 140a, 140b, the operator begins to compress one or all of the subactuators 160a, 160b toward the body 110 by applying a compressive force onto one or all of the subactuators 160a, 160b. In the case where the user desires to release only a portion of the total available antiseptic solution, the user will apply compressive force only on one of the subactuators 160a, 160a. In the case where the user desires to release all of the available antiseptic solution, the user will apply compressive force on both of the subactuators 160a, 160b. As the subactuators 160a, 160b begin to move toward the body 110, the contact points 152a, 152b begin to apply pressure on the body 110. This pressure then applies pressure on the ampoules 140a, 140b. Once sufficient compressive force is imparted at the contact points 152a, 152b, the ampoules 140a, 140b fracture, thereby releasing flow of the fluid contained therein. FIG. 7 shows a cross sectional view after the actuator 160 has been depressed. As shown in FIG. 7, the body 110 has been flexed inwardly such that the angle 156b between the lever and the body 110 has decreased relative to the angle 156a shown in FIG. 6 prior to actuation. Angle 156b may be about 5 to 10 degrees smaller than angle 156a.

In the case where the user is applying pressure to only the subactuator 160a, only the first contact point 152a will contact the body 110 and only the corresponding first ampoule 140a will rupture. FIG. 8 shows a rear view of the applicator 100 when only one subactuator 160a has been actuated. As shown in FIG. 8, the subactuator 160a is at a lower height than subactuator 160b, which remains at the pre-actuation position. In this arrangement, only ampoule 140a would be ruptured. While subactuator 160a is illustrated as being actuated in FIG. 8, in another aspect subactuator 160b could be actuated first. When the user subsequently needs more solution to be released, the user can then independently apply pressure on the second subactuator 160b, causing the second contact point 152b to contact the body, and thereby rupturing the second ampoules 140b. FIG. 9 shows a rear view of the applicator 100 after the subactuator 160b has been actuated following the actuation of subactuator 160a. As shown in FIG. 9, both the subactuators 160a, 160b are at the relatively lowered height and both ampoules 140a, 140b would be ruptured. In the case where the user wants to release all of the solution at once, the user may contemporaneously apply pressure to both the subactuators 160a, 160b, thereby fracturing both ampoules 140a, 140b. FIG. 9 also shows what the applicator looks like after contemporaneous actuation.

After rupturing at least one of the ampoules 140a, 140b, the solution will drain from the ampoules 140a, 140b into the fluid chamber 170 under its own weight. After passing through the pledget 180 and becoming tinted (if a tint is present in the pledget), the fluid flow passes into the fluid chamber 170. The solution may then soak into, or otherwise flow through, the application member 120. The fluid chamber 170 may serve to accumulate and distribute the solution evenly over substantially the entire area of the application member 120. Once the application member 120 is engorged, for example, the solution may then be applied to a patient by wiping the distal surface of the application member 120 against the skin. In the case where the user has only ruptured one of the ampoules 140a, 140b, the user may then rupture the second ampoule and the solution will flow in the same manner as described above.

While two subactuators and two ampoules have been described, as noted above, it should be understood that the same principle of independent actuation may be applied to any number of subactuators and ampoules to give the user a greater control over how much fluid is released. For example, if four ampoules and four subactuators were implemented, the user would have the option to release the solution one ampoule at a time up to four times. Furthermore, while the subactuators are illustrated as a generally single actuator that is split into two, it should be understood that the same principle can be applied in which two completely separate actuators that are placed on opposing sides of the body.

FIGS. 10-13 show an applicator assembly 200 in accordance with other aspects of the present invention. The applicator assembly 200 is similar to the applicator assembly 100 discussed above and similar elements have similar reference numbers.

Figure 10:
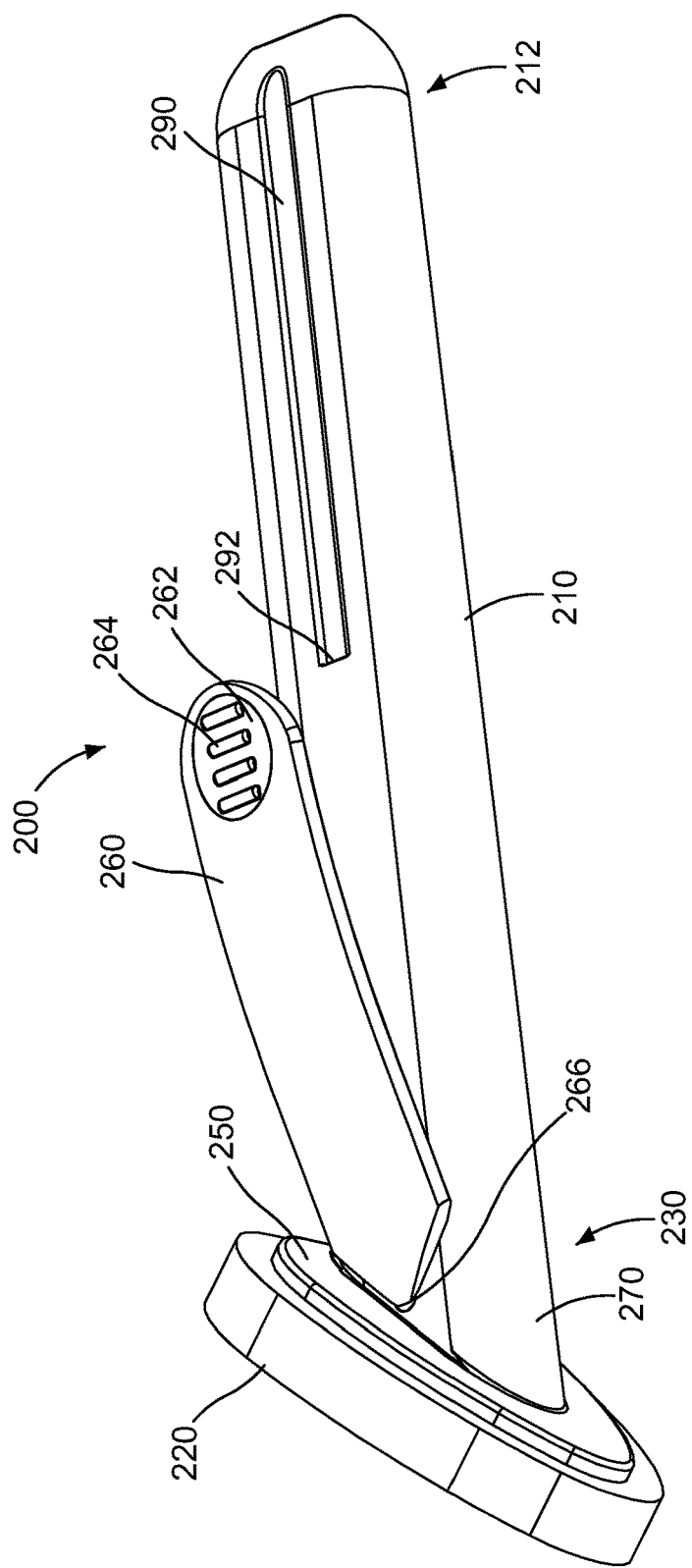
FIG. 10 is a perspective view of an antiseptic applicator assembly in accordance with other aspects of the present invention.
Figure 11:
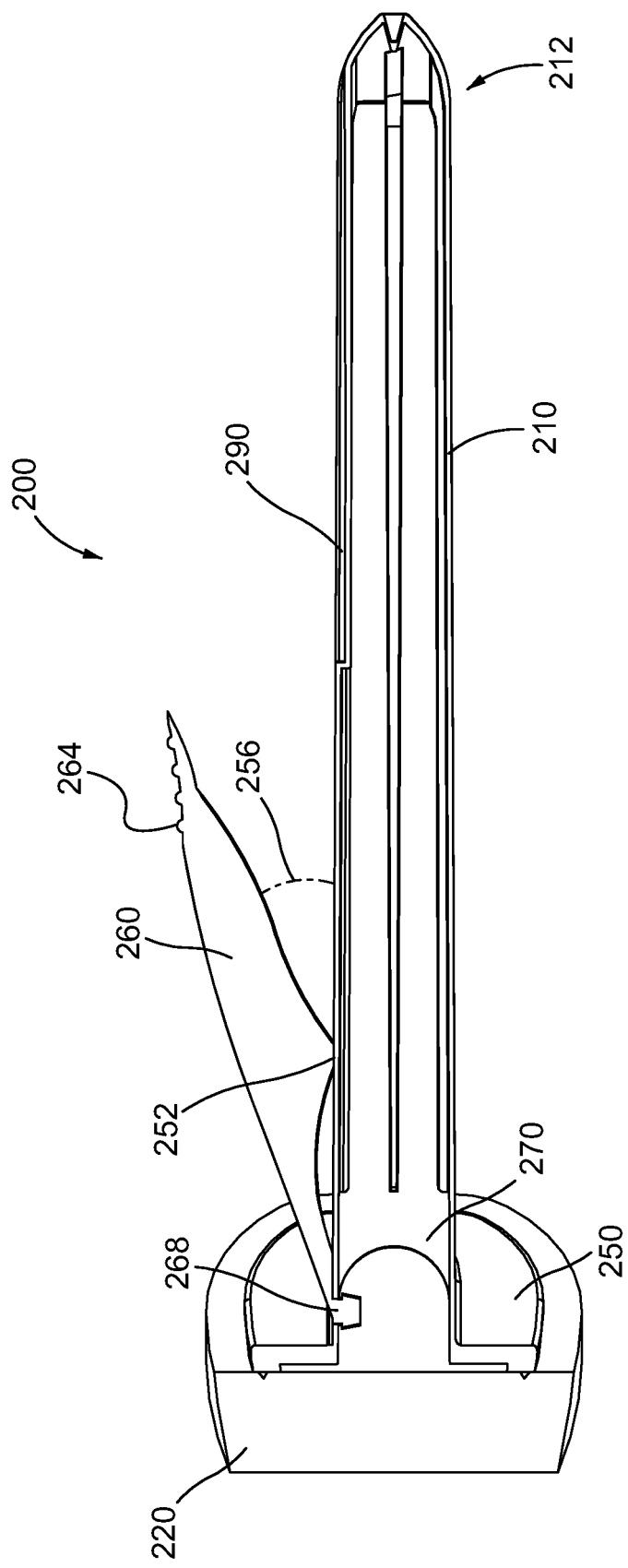
FIG. 11 is a cross section view of the applicator assembly of FIG. 10.

FIG. 10 shows a perspective view of the applicator assembly 200 prior to actuation to release fluid. FIG. 11 shows a cross section view of the applicator assembly 200, with the internal components, e.g., the ampoules and pledget, omitted. The antiseptic applicator 200 may comprise a substantially hollow body 210, an application member 220 mounted to a distal end portion 230 of the body 210, and a plurality of ampoules received within the body 210. The internal components, e.g., the ampoules and pledget, of the applicator assembly 200 are not illustrated and would be the same as the internal components of applicator assembly 100 discussed above. The application member 220 may be made as the same material as discussed above. The body 210 may include a mounting flange 250, as above.

The applicator 200 also includes an actuator 260. As shown in FIG. 11, the actuator 260 may include a pivot mechanism 268 configured to allow the user to pivot the actuator 260 transversely relative to a longitudinal axis of the body 210. The pivot mechanism may extend into the body 210 via a through hole 266 (FIG. 10). The actuator may include a dimple 262 having a shape congruent to a human thumb as described above. The dimple 262 may include a plurality of ridges 264 as described above. The pivot mechanism 268 allows the user to independently fracture the ampoules disposed within the body 210. As shown in FIGS. 10-13, the actuator 260 may comprise a lever. As shown in FIGS. 10-13 the actuator 260 may project from a side portion of body 210. However, it will be appreciated that actuator 260 may project from any portion of body 210 as long as it is aligned with ampoules. As best seen in FIG. 11, the actuator 260 may include a contact point 252 may apply a compressive force to the body 210 when the actuator 260 is actuated. As will be discussed in more detail below, by pivoting the actuator 260 via the pivot mechanism 268, the contact point 252 can be aligned with only one of the ampoules.

The actuator 260, prior to actuation may extend at an angle 256 (FIG. 11) toward the proximal end 212 of the body 210 (e.g., the free end of the actuator/subactuators may be located closer to the proximal end of the body than the portion of the actuator connected to the body) such that when the actuator 260 is actuated (i.e., pressed toward the body 210), the contact point 252 applies compressive pressure to the body 210. The angle 256 may be the same as discussed above. As will be described in more detail below, in an aspect of the present invention, the actuator 260 and the contact point 252 may be configured (e.g., positioned and angled) such that, the user may choose to rupture only one of the ampoules independently of the other ampoule or choose to rupture both of the ampoules together.

With the ampoules mounted in the body 210, as described above, and the application member 220 mounted to close off the distal end portion 230 of the body 210, a fluid chamber 270 may be formed that extends between the application member 220 and the ampoules. As noted above a fluid metering device, such as a pledget (not shown), may be provided in the fluid chamber 270 to further control and/or direct the flow of solution from the ampoules when the assembly 200 is in use. The pledget may be the same as discussed above. As shown in FIGS. 10 and 11, the applicator 200 may include a trench 290 formed through the body 210. The trench 290 may be the same as discussed above including the vent hole 292 (FIGS. 12 and 13) and the surface 294 (FIGS. 12 and 13).

Figure 12:
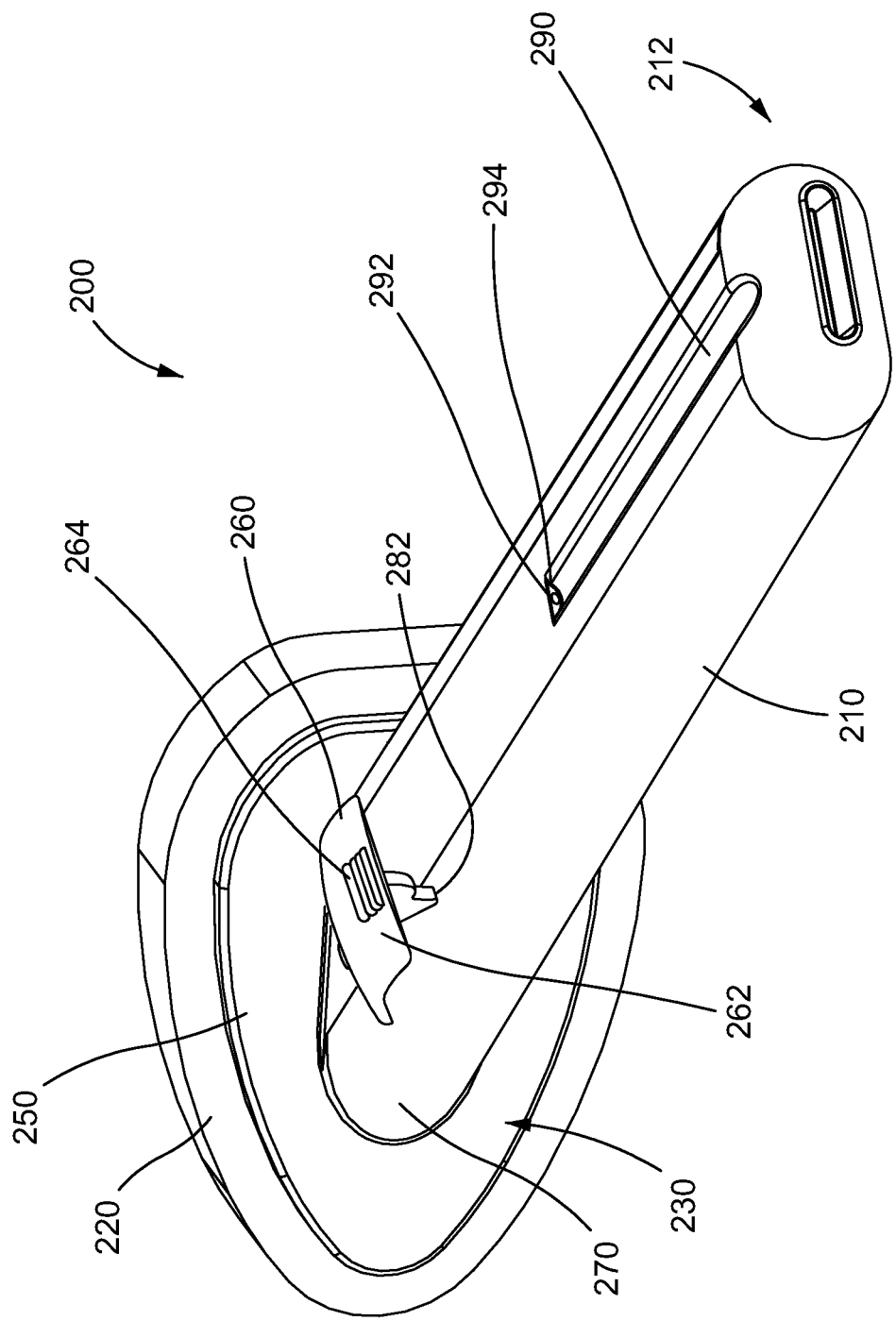
FIG. 12 is a perspective view the of the applicator assembly of FIG. 10 in a first orientation.
Figure 13:
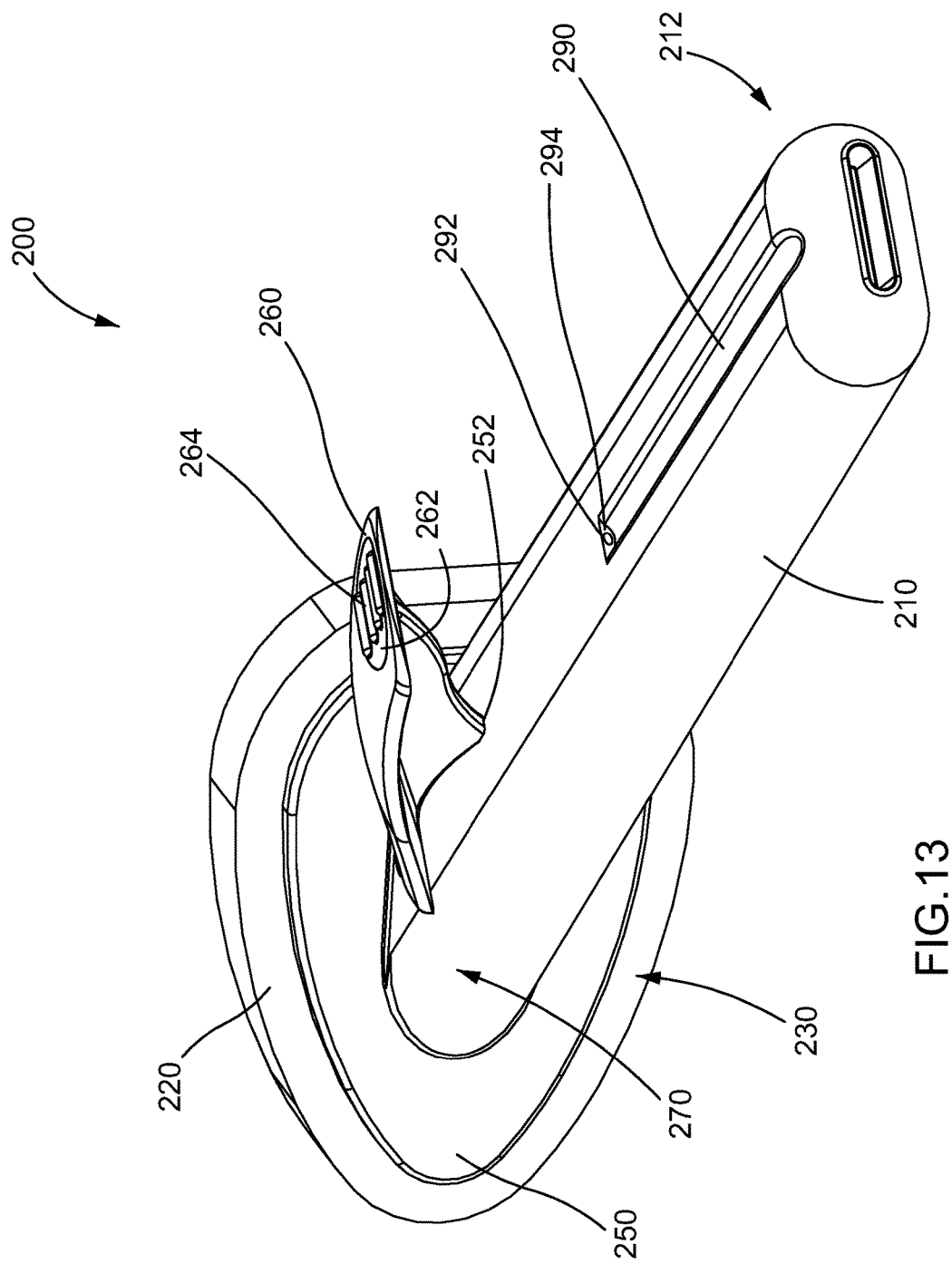
FIG. 13 is a perspective view of the applicator assembly of FIG. 10 in a second orientation.

Actuation of the assembly 200 will now be described with reference to FIGS. 10-13. Activation of the applicator 200 to release the solution and control the flow may be achieved by one handed actuation of the actuator 260. To operate the applicator 200, the operator first grasps the body 210. Depending on the desired release of fluid, the user may pivot the actuator 260 via the pivot mechanism 268 to align the contact point 252 with only one of the ampoules or to align it with both of the ampoules. FIGS. 11 and 13 show the orientation where the actuator 260 is aligned with both of the ampoules. That is, in FIGS. 11 and 13, the contact point 252 is approximately placed at the midpoint between the two ampoules. FIG. 10 shows the orientation where the actuator 260 is aligned with only one of the ampoules (e.g., the right ampoule), while FIG. 12 shows the orientation where the actuator 260 is aligned with only the other one of the ampoules (e.g., the left ampoule). That is, in FIGS. 10 and 12, the contact point 252 is positioned such that the application of force will only impact one of the ampoules.

Generally, the default/starting position (i.e., the position in which the device is delivered to the user) will be the dual actuation position shown in FIGS. 11 and 13. The user may first choose whether to move the actuator 260 depending on the amount of fluid that the user desires to release. If the user desires to break only one of the ampoules to release an initial amount of fluid, the user will first pivot the actuator 160 to one of the position shown in FIGS. 10 and 12. The user may then place the thumb on the actuator 260. The dimple 262 and the ridges 164 may assist the user in locating the proper placement of the thumb, as discussed above. As also noted above, the user my grip the actuator with the palm of the hand. The operator may then begin to compress the actuator 260 toward the body 210 by applying a compressive force onto the actuator 260. Rupturing the ampoule is the same as discussed above.

After rupturing one of the ampoules, the user may want to subsequently release the fluid from the other ampoule. When the user needs more solution to be released, the user can then pivot the actuator 260 via the pivot mechanism 268 until the contact point 252 of the actuator is aligned with the other one of the ampoules. The user may then repeat the compressive action discussed above thereby causing the rupturing the second ampoule.

Alternatively, when the user desires to rupture both ampoules at the same time, the user may pivot the actuator 260 to approximately the position shown in FIGS. 11 and 13. As long as the contact point 252 is substantially centered the application of compressive force will act on both ampoules. As noted above, the default orientation is generally the position shown in FIGS. 11 and 13, in which case pivoting of the actuator 260 may not be necessary if simultaneously rupturing of the ampoules is desired.

After rupturing one or more of the ampoules, the solution will drain from the ampoules into the fluid chamber 270 and may ultimately applied to the patient in the same manner as discussed above with respect to the applicator 100.

While two ampoules have been described, as noted above, it should be understood that the same principle of independent actuation may be applied to any number of ampoules to give the user a greater control over how much fluid is released. For example, if four ampoules were implemented, the user would have the option to release the solution one ampoule at a time by pivoting the actuator 260 to align with each of the four ampoules in succession (or multiple at a time).

Figure 14:
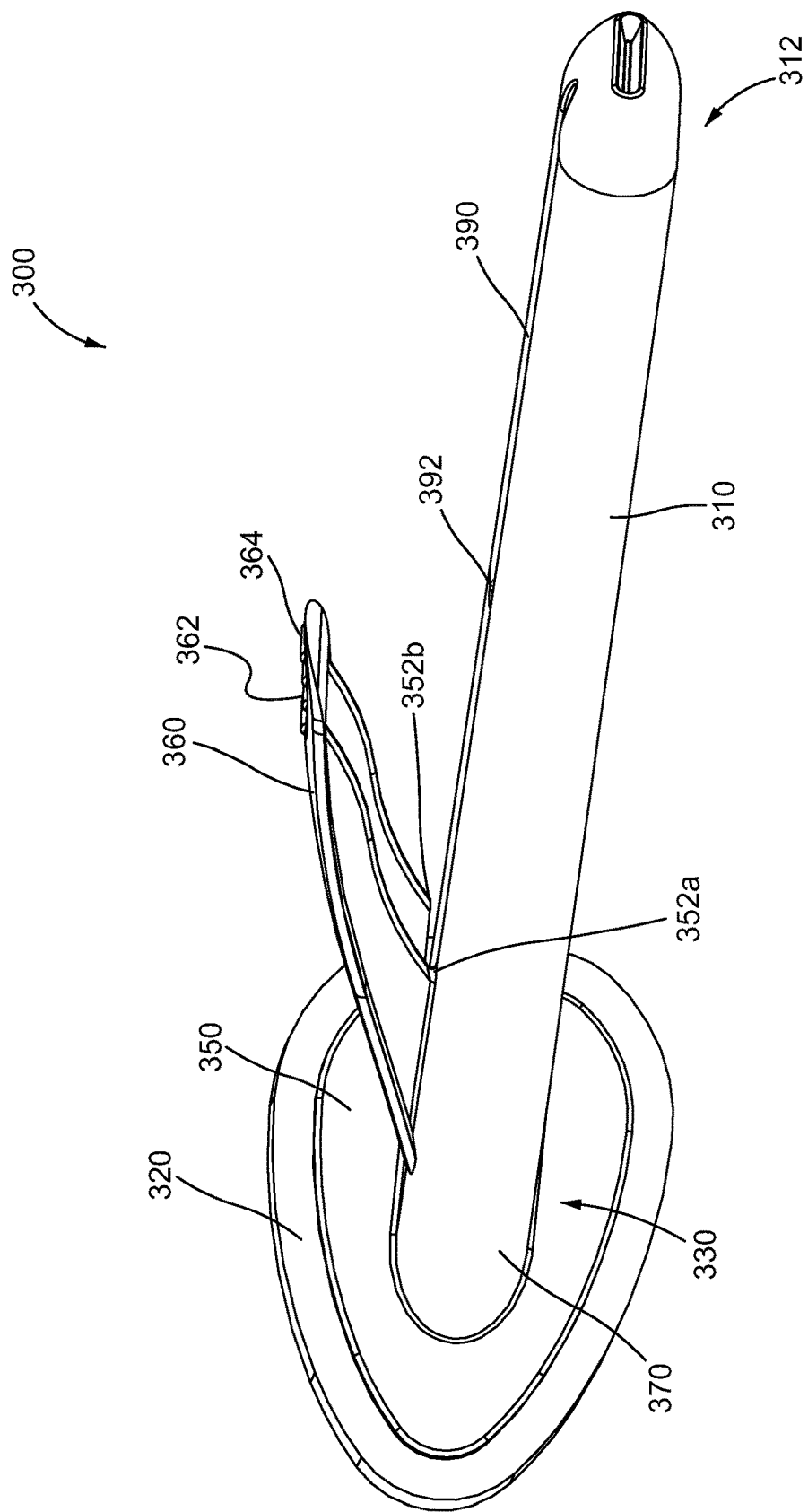
FIG. 14 is a perspective view of an antiseptic applicator assembly in accordance with other aspects of the present invention.

FIG. 14 shows an applicator assembly 300 in accordance with other aspects of the present invention. The applicator assembly 300 is similar to the applicator assembly 100 discussed above and similar elements have similar reference numbers.

FIG. 14 shows a perspective view of the applicator assembly 300 prior to actuation to release fluid. The antiseptic applicator 300 may comprise a substantially hollow body 310, an application member 320 mounted to a distal end portion 330 of the body 310, and a plurality of ampoules received within the body 310. The internal components, e.g., the ampoules and pledget, of the applicator assembly 300 are not illustrated and would be the same as the internal components of applicator assembly 100 discussed above. The application member 320 may be made as the same material as discussed above. The body 310 may include a mounting flange 350, as above.

The applicator 300 also includes an actuator 360. As shown in FIG. 14, the actuator 360 may include two distinct contact points 352a, 352b on opposing sides of the actuator 360. The first contact point 352a may be in contact with the body 310 prior to actuation while the second contact point 352b may be spaced away from the body 310 prior to actuation. The first contact point 352a is aligned with one of the ampoules within the body 310 while the second contact point 352b is aligned with the second of the ampoules within the body 310. The two differently spaced contact points 352a, 352b allows the user to independently fracture the ampoules disposed within the body 310, which is discussed below. The actuator 360 may include a dimple 362 having a shape congruent to a human thumb as described above. The dimple 362 may include a plurality of ridges 364 as described above. The actuator 360 may comprise a lever. As shown in FIG. 14 the actuator 360 may project from a side portion of body 310. However, it will be appreciated that actuator 360 may project from any portion of body 310 as long as it is aligned with ampoules.

The actuator 360, prior to actuation may extend at an angle toward the proximal end 312 of the body 310 (e.g., the free end of the actuator/subactuators may be located closer to the proximal end of the body than the portion of the actuator connected to the body) such that when the actuator 360 is actuated (i.e., pressed toward the body 310), the contact point 352a and subsequently the second contact point 352b applies compressive pressure to the body 310. The angle may be the same as discussed above. As will be described in more detail below, in an aspect of the present invention, the actuator 360 and the contact points 352a, 352b may be configured (e.g., positioned and angled) such that, the user may choose to rupture only one of the ampoules independently of others.

With the ampoules mounted in the body 310, as described above, and the application member 320 mounted to close off the distal end portion 330 of the body 310, a fluid chamber 370 may be formed that extends between the application member 320 and the ampoules. As noted above a fluid metering device, such as a pledget (not shown), may be provided in the fluid chamber 370 to further control and/or direct the flow of solution from the ampoules when the assembly 300 is in use. The pledget may be the same as discussed above. As shown in FIG. 14, the applicator 300 may include a trench 390 formed through the body 310. The trench 390 may be the same as discussed above including the vent hole 392 and the surface (not shown).

Actuation of the assembly 300 will now be described. Activation of the applicator 300 to release the solution and control the flow may be achieved by one handed actuation of the actuator 360. To operate the applicator 300, the operator first grasps the body 310. The user may then place the thumb on the actuator 360. The dimple 362 and the ridges 364 may assist the user in locating the proper placement of the thumb, as discussed above. As also noted above, the user my grip the actuator with the palm of the hand. The operator may then begin to compress the actuator 360 toward the body 310 by applying a compressive force onto the actuator 360. As compressive force is applied to the actuator 360 the first contact point 352a will begin to apply pressure to the body 310 and rupture only the ampoule aligned with the first contact point 352a. Because the second contact point 352b, which is aligned with the second ampoule, is spaced from the body 310, the initial compressive force has no impact on the second ampoule. That is, until the user provides enough compressive force to close the space between the second contact point 352b and the body 310, the compressive force is not being applied to the portion of the body 310 that would impact the second ampoule. For this reason, the applicator 300 may also be referred herein as a staggered applicator.

After rupturing the first one of the ampoules, the user may want to subsequently release the fluid from the other ampoule. The user can choose how long to wait before proceeding with releasing the fluid from the second ampoule. When the user needs more solution to be released, the user may increase the compressive force being applied to the actuator 360 beyond what was necessary to rupture the first ampoule. The increase in compressive force will close the spacing between the second contact point 352b and the body 310 as the actuator 350 continues to pivot closer to the body. Once the second contact point 352b contacts the body 310, the continuing increase in compressive force on the actuator 360 will now cause the body 310 to deform and rupture the second ampoule in the same manner discussed above with respect to the applicator 100. In this manner the user can release fluid from the first ampoule and then independently release fluid from the second ampoule at the desired time.

Alternatively, when the user desires to rupture both ampoules at substantially the same time, the user may apply maximum compressive force in one swift motion. That is, with one strong single compression, the same release of fluid will occur as discussed above. However, because the compression occurs in one single quick motion, the second ampoule will rupture within a second or two following the rupturing of the first ampoule. In this manner, the time between rupturing is so short that, from the perspective of the user, the rupturing is essentially contemporaneous. Thus, with the applicator 300, the user similarly has the ability to independently rupture the ampoules or contemporaneously rupture the ampoules.

After rupturing one or more of the ampoules, the solution will drain from the ampoules into the fluid chamber 370 and may ultimately applied to the patient in the same manner as discussed above with respect to the applicator 100.

While two ampoules have been described, as noted above, it should be understood that the same principle of independent actuation may be applied to any number of ampoules to give the user a greater control over how much fluid is released. For example, if four ampoules were implemented, the user would have the option to release the solution, one ampoule at a time, by having an actuator with four distinct contact points, each subsequent contact point being spaced farther from the body than the contact point before it.

Figure 15:
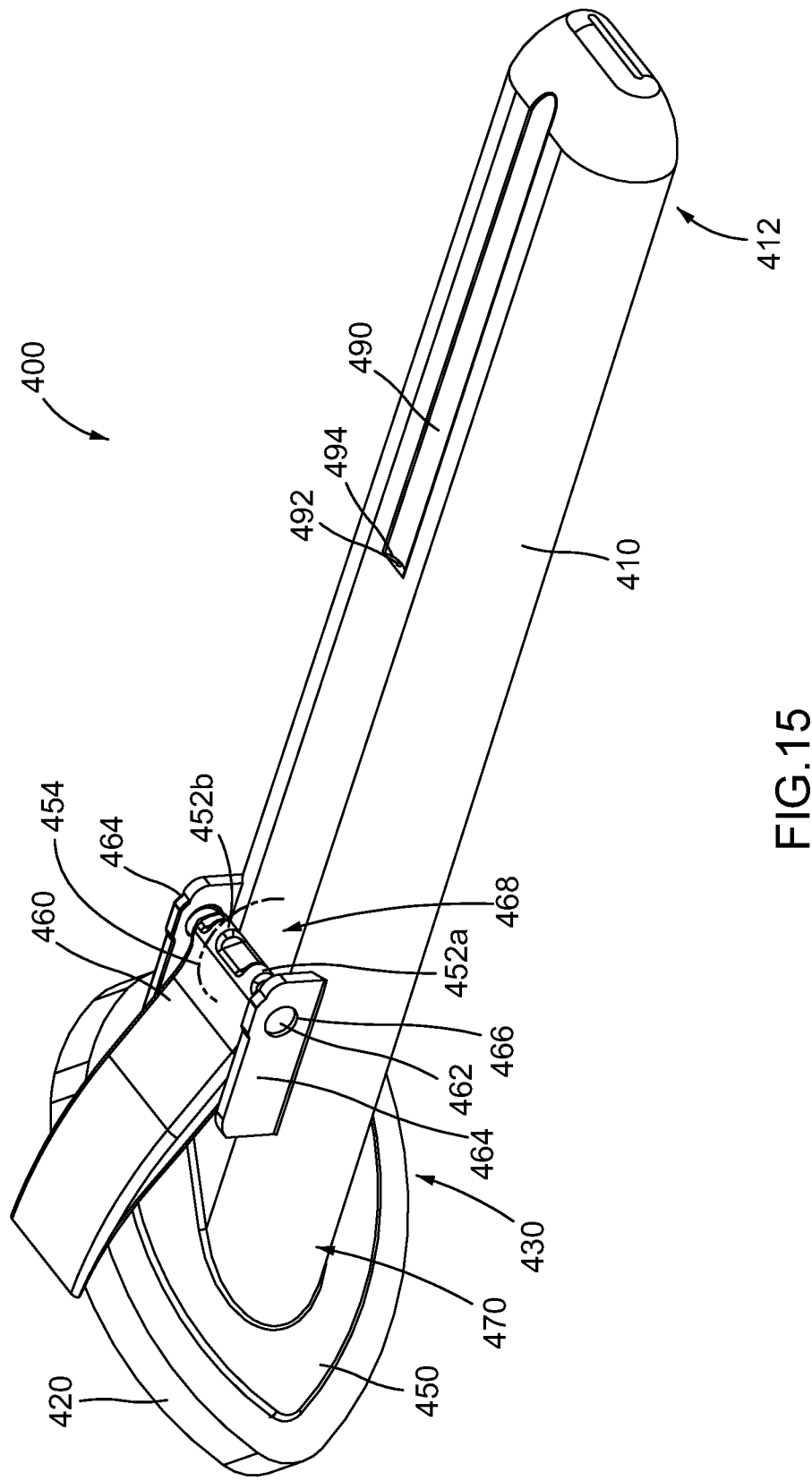
FIG. 15 is a perspective view of an antiseptic applicator assembly in a first orientation in accordance with other aspects of the present invention.
Figure 16:
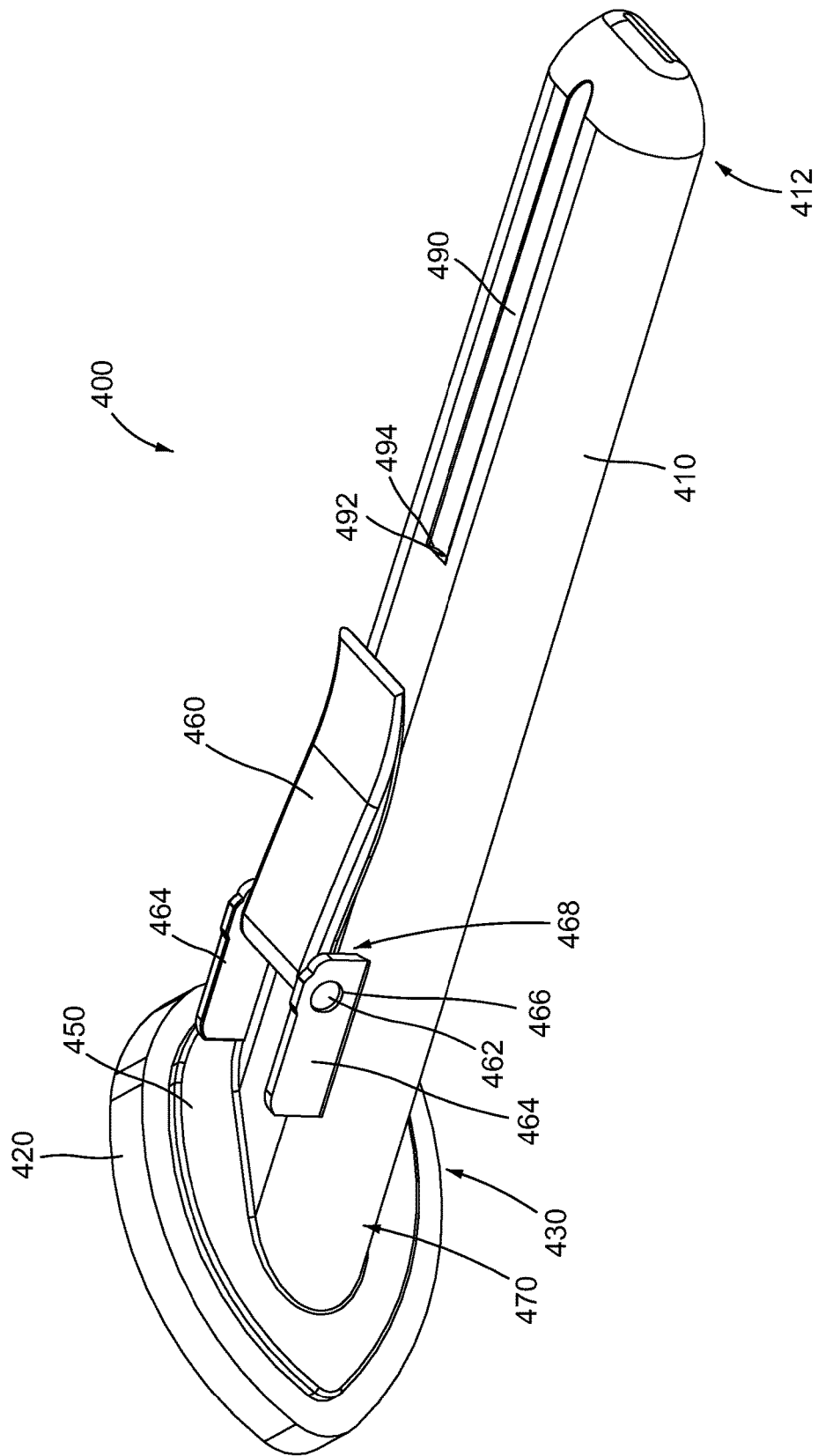
FIG. 16 is a perspective view the applicator assembly of FIG. 15 in a second orientation.

FIGS. 15 and 16 show an applicator assembly 400 in accordance with other aspects of the present invention. The applicator assembly 400 is similar to the applicator assembly 100 discussed above and similar elements have similar reference numbers.

FIG. 15 shows a perspective view of the applicator assembly 400 prior to actuation to release fluid. FIG. 15 shows a perspective view of the applicator assembly 400 after actuation to release fluid. The antiseptic applicator 400 may comprise a substantially hollow body 410, an application member 420 mounted to a distal end portion 430 of the body 410, and a plurality of ampoules received within the body 410. The internal components, e.g., the ampoules and pledget, of the applicator assembly 400 are not illustrated and would be the same as the internal components of applicator assembly 100 discussed above. The application member 420 may be made as the same material as discussed above. The body 410 may include a mounting flange 450, as above.

The applicator also includes an actuator 460 and a hinge mechanism 468 allowing the actuator 460 to rotate relative to the body 410. The actuator 460 may include a pair of rotation elements 462, forming part of the hinge mechanism 468. As shown in FIGS. 15 and 16, the rotation elements 462 may be coupled with opposing retaining posts 464. Each retaining post may include a through hole 466 for rotatably receiving one of the rotation elements 462. Thus, the retaining posts 464 and the through holes 466 form a portion of the hinge mechanism 468. Because of this coupling forming the hinge mechanism 468, it is possible to rotate the actuator 460 from the unactuated position shown in FIG. 15 to the actuated position shown in FIG. 16, which is discussed in more detail below.

As shown in FIG. 15, the actuator 460 may include two projections 452a, 452b that define two distinct contact points on opposing sides of the actuator 460. As shown in FIG. 15, the first and second projections 452a, 452b are not in contact with the body 410 prior to actuation. However, the projections 452a, 452b are positioned along the hinge mechanism 468 such that the first projection 452a is aligned with one of the ampoules within the body 410 and the second projection 452b is aligned with the second of the ampoules within the body 410. Furthermore, prior to actuation, in a first position, the actuator 460 extends obliquely away from the body 410 thereby causing the applicator to have a relatively large profile. While not shown, the actuator 460 may include a dimple and plurality of ridges as described above. The actuator 460 may comprise a lever. As shown in FIG. 15, the actuator 460 may project from a side portion of body 410. However, it will be appreciated that actuator 460 may project from any portion of body 410 as long as the projections are aligned with ampoules.

As noted above, the actuator 460, prior to actuation may extend obliquely relative to the body 410. More particularly, the actuator 460 may extend an angle 454 toward the distal end 430 of the body 410 (e.g., the free end of the actuator may be located closer to the distal end of the body than the portion of the actuator connected to the body) such that when the actuator 460 is actuated (i.e., rotated toward the body 410), the projections 452a, 452b contact the body 410 and impart a compressive pressure to the body 410. The angle 454 may be from about 90 degrees to about 160 degrees, more preferably about 105 degrees to about 145 degrees. In an aspect of the present invention, the actuator 460 and the contact points 452a, 452b may be configured (e.g., positioned and angled) such that, upon actuation, both of the ampoules within the body 410 are ruptured.

With the ampoules mounted in the body 410, as described above, and the application member 420 mounted to close off the distal end portion 430 of the body 410, a fluid chamber 470 may be formed that extends between the application member 420 and the ampoules. As noted above a fluid metering device, such as a pledget (not shown), may be provided in the fluid chamber 470 to further control and/or direct the flow of solution from the ampoules when the assembly 400 is in use. The pledget may be the same as discussed above. As shown in FIGS. 15 and 16, the applicator 400 may include a trench 490 formed through the body 410. The trench 490 may be the same as discussed above including the vent hole 492 and the surface 494.

Actuation of the assembly 400 will now be described. Activation of the applicator 400 to release the solution and control the flow may be achieved by one handed actuation of the actuator 460. To operate the applicator 400, the operator first grasps the body 410. The user may then place the thumb on the actuator 460. Dimples and ridges (not shown) may assist the user in locating the proper placement of the thumb, as discussed above. As also noted above, the user my grip the actuator with the palm of the hand. The operator may then begin to rotate the actuator 460 toward the body 410 via the hinge mechanism 468 by applying rotational force onto the free end of the actuator 460. Due to the coupling of the rotation projection 462 of the actuator 460 with the holes 466 of the retaining posts 464 to form the hinge mechanism 468, the application of force at the free end of the actuator 460 will cause the actuator 460 to rotate about the rotation projection 462. As the actuator 460 rotates, the first and second projections 452a, 452b will come into contact with and begin to apply pressure onto the body 410. The applied pressure becomes greater as the user continues to rotate the actuator due to the height of the projection members 452a, 452b. The application of pressure from the projection members 452a, 452b, will cause the ampoules aligned with the projection members 452a, 452b to rupture. The solution will then drain from the ampoules into the fluid chamber 470 and may ultimately applied to the patient in the same manner as discussed above with respect to the applicator 100.

After rupturing the ampoules, the user can continue to rotate the actuator 460 to a second position where it is comes into contact with the body 410. This orientation is shown in FIG. 16. As shown in FIG. 16, the actuator 460 may be fully rotated until it contacts the body 410. That is, in the fully rotated position, the actuator 460 extends along the body 410 substantially parallel to a longitudinal axis of the body. For example, the actuator may be substantially flush with the body 410 in the second position. As shown in FIG. 16, the overall profile of the applicator 400 is greatly reduced in the fully actuated/second position as compared to the pre-actuation/first position. Having a smaller profile makes it easier for the user to reach areas of the patient that are not otherwise accessible when the profile is relatively large.

While two ampoules have been described, it should be understood that the only one or more than two ampoules may be used. When only one ampoule is used the actuator need only have one projection member. When more than two ampoules are used the actuator may have a number of projection members equal to the number of ampoules. In yet another aspect, the actuation member may have a single projection or a number of projection members less than the number ampoules so long as the projection member or members are have sufficient size to rupture all the ampoules in the body.

Figure 17:
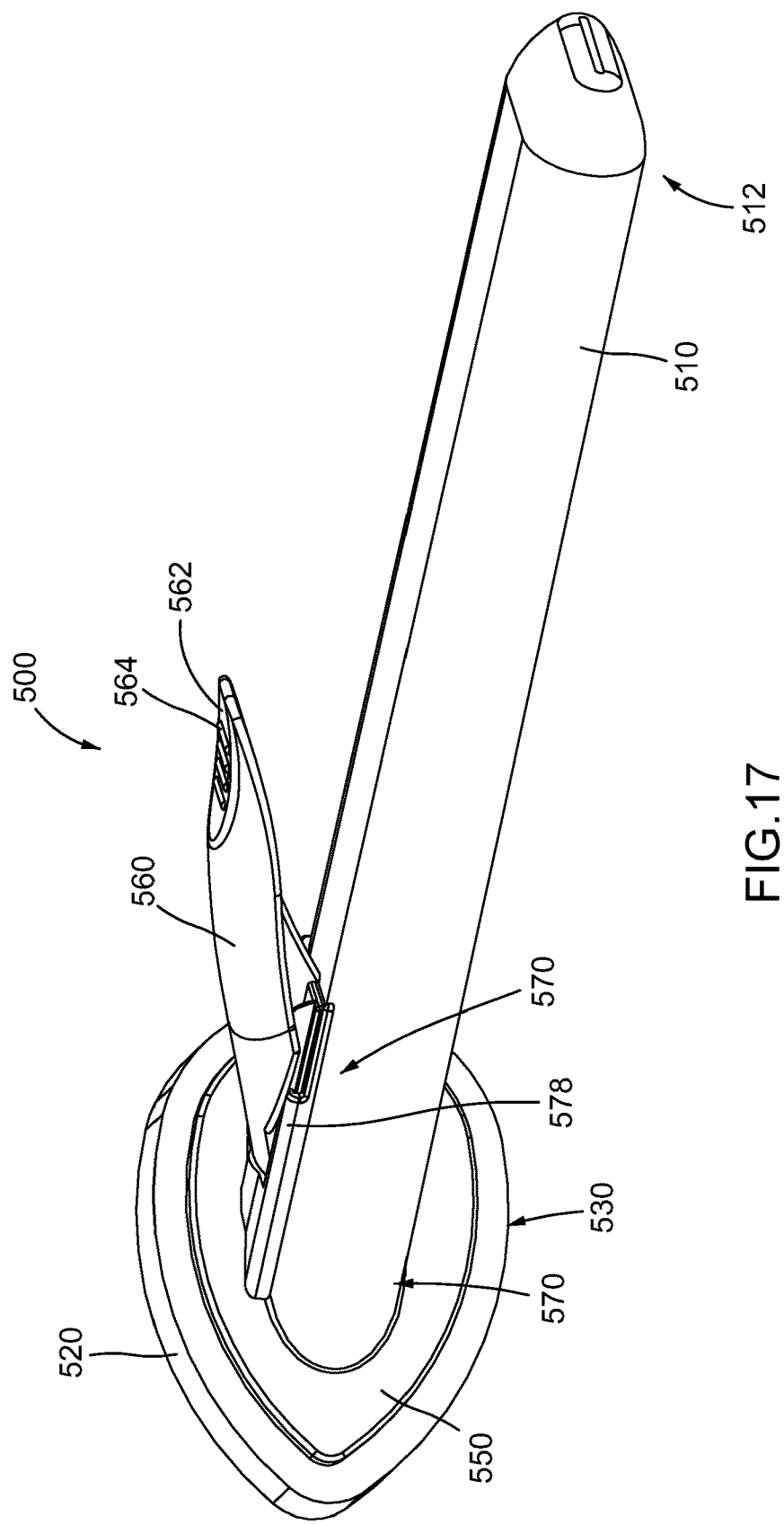
FIG. 17 is a perspective view of an antiseptic applicator assembly in a first orientation in accordance with other aspects of the present invention.
Figure 18:
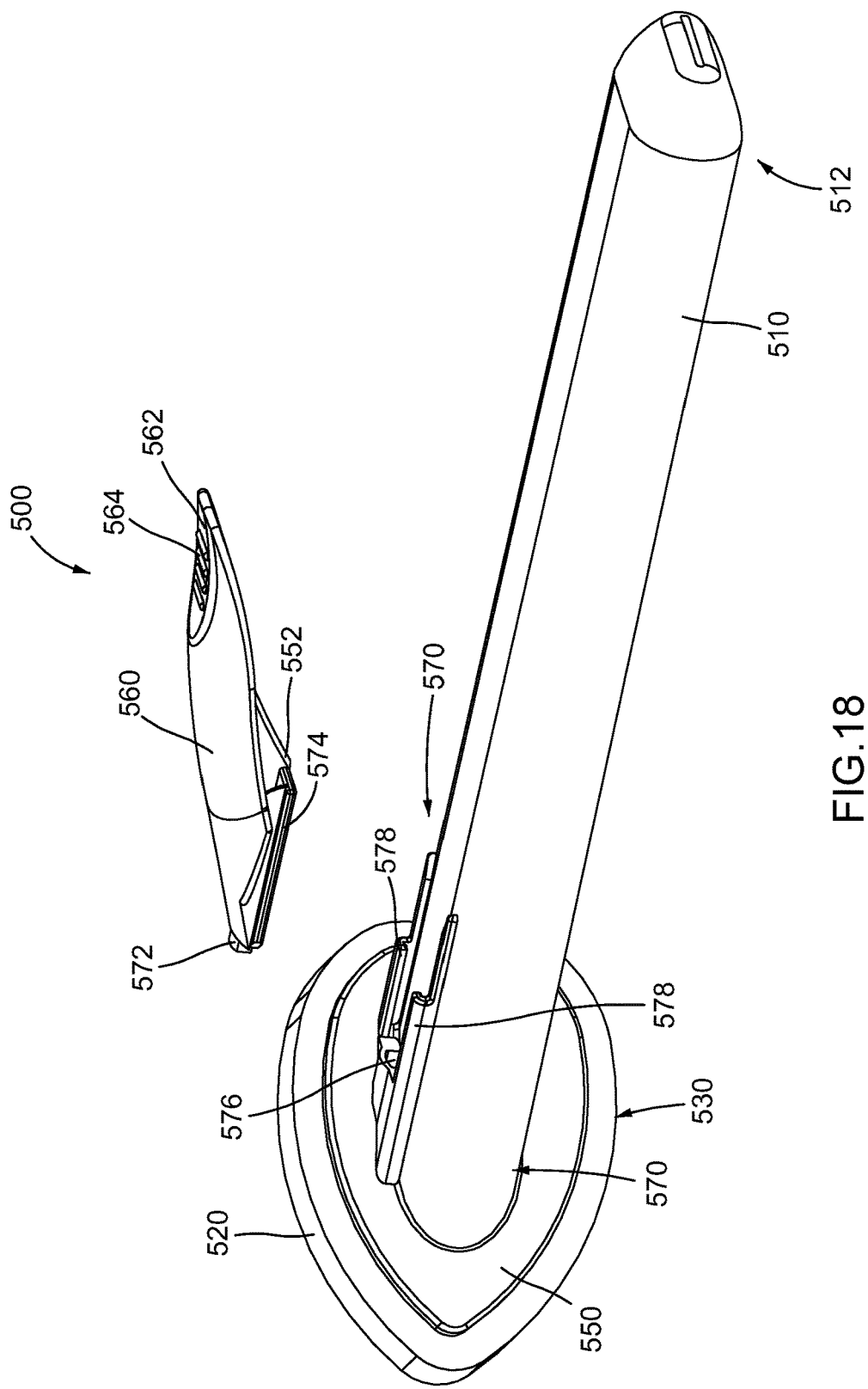
FIG. 18 is a perspective view the applicator assembly of FIG. 17 in a second orientation.

FIGS. 17 and 18 show an applicator assembly 500 in accordance with other aspects of the present invention. The applicator assembly 500 is similar to the applicator assembly 100 discussed above and similar elements have similar reference numbers.

FIG. 17 shows a perspective view of the applicator assembly 500 prior to actuation to release fluid. FIG. 18 shows a perspective view of the applicator assembly 500 after actuation to release fluid. The antiseptic applicator 500 may comprise a substantially hollow body 510, an application member 520 mounted to a distal end portion 530 of the body 510, and a plurality of ampoules received within the body 510. The internal components, e.g., the ampoules and pledget, of the applicator assembly 500 are not illustrated and would be the same as the internal components of applicator assembly 100 discussed above. The application member 520 may be made as the same material as discussed above. The body 510 may include a mounting flange 550, as above.

The applicator 500 also includes an actuator 560 and a coupling mechanism 570 allowing the applicator 560 to be removably coupled to the body 510. The actuator 560 may include a projection member 572 (FIG. 18) and lateral ribs 574, each forming part of the coupling mechanism 570. As shown in FIGS. 17 and 18, the projection member 572 may shaped to fit within a receiving member 576 formed on a surface of the body 510. Furthermore, the ribs 574 may be shaped fit within corresponding lips 578 also formed on a surface of the body 510. Thus, the receiving member 576 and the lips 578 may serve as female members for coupling with the projection member 572 and ribs 574, which serve as male members. The features together form the coupling mechanism 570. While the female features are shown as part of the body 510 and the male features are shown as part of the actuator 560, it should be understood that the male/female relationship may be reversed. Because of the coupling between the actuator 560 and the body 512, it is possible to entirely remove the actuator 560 from the body 510 after actuation (FIG. 18), which is discussed in more detail below.

As shown in FIG. 18, the actuator 560 may include a contact point 552 that is located along the body 510 such that actuation of the actuator will cause one or more ampoules in the body to rupture. Actuation of the actuator is the same as discussed above, where application of compressive force on the actuator 560 will case the contact point 552 to deform the body 510 and eventually rupture the ampoules contained therein. The actuator 560 may include a dimple 562 and plurality of ridges 564 as described above. The actuator 560 may comprise a lever. As shown in FIG. 17, the actuator 560 may project from a side portion of body 510. However, it will be appreciated that actuator 560 may project from any portion of body 510 as long as the contact point 552 is aligned with the ampoules.

The actuator 560, prior to actuation and in a first position, may extend at an angle toward the proximal end 512 of the body 510 (e.g., the free end of the actuator may be located closer to the proximal end of the body than the portion of the actuator connected to the body) such that when the actuator 560 is actuated (i.e., pressed toward the body 510), the contact point 552 applies compressive pressure to the body 510. The angle may be the same as discussed above with respect to the applicator 100. In an aspect of the present invention, the actuator 560 and the contact point 552 may be configured (e.g., positioned and angled) such that, upon actuation, both of the ampoules within the body 510 are ruptured.

With the ampoules mounted in the body 510, as described above, and the application member 520 mounted to close off the distal end portion 530 of the body 510, a fluid chamber 570 may be formed that extends between the application member 520 and the ampoules. As noted above a fluid metering device, such as a pledget (not shown), may be provided in the fluid chamber 570 to further control and/or direct the flow of solution from the ampoules when the assembly 500 is in use. The pledget may be the same as discussed above. While not shown, the applicator 500 may include a trench formed through the body 510, including the vent hole and the surface discussed above.

Actuation of the assembly 500 will now be described. Activation of the applicator 500 to release the solution and control the flow may be achieved by one handed actuation of the actuator 560. To operate the applicator 500, the operator first grasps the body 510. The user may then place the thumb on the actuator 560. A dimple 562 and ridges 564 may assist the user in locating the proper placement of the thumb, as discussed above. As also noted above, the user my grip the actuator with the palm of the hand. The operator may then compress the actuator 560 toward the body 510 in the same manner as discussed above with respect to the applicator 100. As the actuator 500 is compressed, the contact point 552 will come into contact with and begin to apply pressure onto the body 510 and eventually cause the ampoules to rupture. The solution will then drain from the ampoules into the fluid chamber 570 and may ultimately be applied to the patient in the same manner as discussed above with respect to the applicator 100.

After rupturing the ampoules, the user can then proceed to decouple the actuator 560 from the body 510 to move the actuator 560 from the first position to a second decoupled position. This orientation is shown in FIG. 18. As shown in FIG. 18, the actuator 560 may be fully decoupled from the body 510. This may be achieved by the user gripping the actuator 560 and pulling rearward, e.g., toward the proximal end 512. This application of force will allow the ribs 574 to slide out of the lips 578 and the projection member 572 to slide out of the receiving member 576. As shown in FIG. 18, once the actuator 560 has been decoupled from the body 510, the overall profile of the applicator 500 is greatly reduced as compared to the pre-actuation/first position. The decoupled/second position can be any location external to the applicator 500. For example, the actuator can be completely discarded to a waste container or placed on an instrument surface. Having a smaller profile makes it easier for the user to reach areas of the patient that are not otherwise accessible when the profile is relatively large.

In another aspect of the present invention, the actuator may have a second coupling mechanism (not shown) that would allow the actuator to hang at a distance from the body. The second coupling mechanism would provide the advantage of reducing the profile of the applicator without risking the possibility of the actuator getting lost after removal. For example a string or similar mechanism may be attached on one end to the body and on the other end to the actuator. Thus, after removing the actuator from the body, the actuator will hang from the body via the second coupling mechanism.

While two ampoules have been described, it should be understood that the only one or more than two ampoules may be used. When only one ampoule is used the actuator need only have one contact point. When more than two ampoules are used the actuator may have a number of contact points equal to the number of ampoules. In yet another aspect, the actuation member may have a single contact point or a number of contact points less than the number ampoules so long as the contact points have sufficient size to rupture all the ampoules in the body.

Various aspects of the present invention have been illustrated as distinct embodiments for clarity. However, it should be understood that all non-mutually exclusive features may be present throughout all of the illustrated embodiments. For example, the removable actuator or the hinge mechanism may be applicable to the applicators 100, 200, 300. Similarly, multiple subactuators (i.e., applicator 100), a pivoting actuator (i.e., applicator 200), or a staggered actuator (i.e., applicator 300) may be implemented in the hinge applicator (i.e., applicator 400) or the removable actuator (i.e., applicator 500). The dimples, ridges, trench, and vent hole may be present in all embodiments.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. An applicator assembly comprising:
   at least two ampoules formed of a frangible material and containing liquid to be applied;
   a container having a proximal end, a distal end, and an interior portion defining a chamber adapted to receive the at least two ampoules;
   an application member attached to the distal end of the container; and
   at least one actuator projecting from the container, wherein the at least one actuator is actuatable to independently fracture the at least two ampoules, thereby independently releasing the liquid into the application member,
   wherein the at least two ampoules comprise an angle therebetween having a fixed value, the fixed value being constant upon actuation of the actuator.

2. The applicator of claim 1, wherein the at least one actuator comprises at least two subactuators, and wherein each of the at least two subactuators is independently acuatable.

3. The applicator of claim 2, wherein the at least two subactuators are contemporaneously actuable.

4. The applicator of claim 2, wherein each of the at least two subactuators is aligned with one of the at least two ampoules.

5. The applicator of claim 2, wherein the subactuators are proximal each other.

6. The applicator of claim 2, wherein each of the subactuators comprise a contact point, and wherein each contact point is aligned with one of the ampoules.

7. The applicator of claim 1, further comprising a pivot mechanism, wherein the at least one actuator is pivotable via the pivot mechanism.

8. The applicator of claim 7, wherein the at least one actuator is pivotable to a first position aligned with a first ampoule of the at least two ampoules and to a second position aligned with a second ampoule of the at least two ampoules.

9. The applicator of claim 1, wherein the at least one actuator comprises a first contact point aligned with a first ampoule of the at least two ampoules and a second contact point aligned with a second ampoule of the at least two ampoules, and wherein the second contact point is spaced from the body prior to actuation of the actuator.

10. The applicator of claim 9, wherein the at least one actuator is configured such that the first contact point imparts compressive force on the first ampoule prior to the second contact point imparting compressive force on the second ampoule during actuation of the actuator.

11. The applicator of claim 1, wherein the at least one actuator is moveable from a first position to a second position, the applicator having a smaller profile when the actuator is in the second position than when the actuator is in the first position.

12. The applicator assembly of claim 1, wherein the at least two ampoules are proximal one another.

* * * * *